(12) United States Patent
Reichen et al.

(10) Patent No.: US 9,011,450 B2
(45) Date of Patent: Apr. 21, 2015

(54) SURGICAL INSTRUMENT

(75) Inventors: Marc Reichen, Oberdorf (CH); Didier Gonzalez, Oberdorf (CH); Martin Schnider, Oberdorf (CH); Joern Richter, Oberdorf (CH)

(73) Assignee: Depuy Synthes Products, LLC, Raynham, MA (US)

( * ) Notice: Subject to any disclaimer, the term of this patent is extended or adjusted under 35 U.S.C. 154(b) by 11 days.

(21) Appl. No.: 13/570,010

(22) Filed: Aug. 8, 2012

(65) Prior Publication Data

US 2014/0046388 A1 Feb. 13, 2014

(51) Int. Cl.
*A61B 17/56* (2006.01)
*A61B 17/70* (2006.01)

(52) U.S. Cl.
CPC .................................. *A61B 17/7083* (2013.01)

(58) Field of Classification Search
CPC ........... A61B 17/7083; A61B 17/7086; A61B 17/7085
USPC ....... 606/86 A, 87, 96, 80, 99, 279, 914, 104, 606/272, 86 R, 270
See application file for complete search history.

(56) References Cited

U.S. PATENT DOCUMENTS

| | | | |
|---|---|---|---|
| 1,710,092 A | 4/1929 | Hitchcock | |
| 2,250,417 A | 7/1941 | Ettinger | |
| 2,333,033 A | 10/1943 | Mraz | |
| 2,373,478 A | 4/1945 | Kuhn | |
| 3,575,405 A | 4/1971 | Harding | |
| 3,861,432 A | 1/1975 | Rothenberger | |
| 4,733,657 A | 3/1988 | Kluger | |
| 4,848,368 A | 7/1989 | Kronner | |
| 4,957,495 A | 9/1990 | Kluger | |
| 5,219,349 A | 6/1993 | Krag et al. | |
| 5,443,467 A | 8/1995 | Biedermann et al. | |
| 5,529,571 A | 6/1996 | Daniel | |
| 5,676,664 A | 10/1997 | Allard et al. | |
| 5,688,276 A | 11/1997 | Shaffer | |
| 5,735,842 A | 4/1998 | Krueger et al. | |
| 5,782,830 A | 7/1998 | Farris | |
| 5,797,900 A | 8/1998 | Madhani et al. | |
| 5,910,141 A | 6/1999 | Morrison et al. | |
| 5,957,927 A | 9/1999 | Magee et al. | |
| 6,102,934 A | 8/2000 | Li | |

(Continued)

FOREIGN PATENT DOCUMENTS

AU 2007/208137 8/2007
DE 3809793 10/1989

(Continued)

OTHER PUBLICATIONS

European Search Report (EP 13178205.4); Nov. 11, 2013.

*Primary Examiner* — Pedro Philogene
(74) *Attorney, Agent, or Firm* — Dunlap Codding, P.C.

(57) ABSTRACT

A surgical instrument for positioning a rod includes a rod holder, a sleeve, and a pusher rod. The rod holder is configured to releasably grip a first end of a rod therebetween. The sleeve is disposed about the rod holder and slideable between an extended position to hold the tines in a rod gripping position and a retracted position to permit release of the rod from the tines. The pusher rod is slidably disposed within the rod holder and has a plurality of rod receiving notches configured to engage the rod such that the rod is held at a selected angle with respect to the pusher rod.

48 Claims, 11 Drawing Sheets

(56) References Cited

U.S. PATENT DOCUMENTS

| | | | |
|---|---|---|---|
| 6,113,605 A | 9/2000 | Storer | |
| 6,120,503 A | 9/2000 | Michelson | |
| 6,156,037 A | 12/2000 | LeHuec et al. | |
| 6,183,472 B1* | 2/2001 | Lutz | 606/86 A |
| 6,224,598 B1 | 5/2001 | Jackson | |
| 6,361,535 B2 | 3/2002 | Jackson | |
| 6,451,019 B1 | 9/2002 | Zucherman et al. | |
| 6,530,929 B1 | 3/2003 | Justis et al. | |
| 6,660,006 B2* | 12/2003 | Markworth et al. | 606/86 A |
| 6,723,100 B2 | 4/2004 | Biedermann et al. | |
| 6,746,443 B1 | 6/2004 | Morley et al. | |
| 6,790,208 B2 | 9/2004 | Oribe et al. | |
| 6,830,574 B2 | 12/2004 | Heckele et al. | |
| 7,011,658 B2 | 3/2006 | Young | |
| 7,223,268 B2 | 5/2007 | Biedermann | |
| 7,250,052 B2 | 7/2007 | Landry et al. | |
| 7,306,603 B2 | 12/2007 | Boehm, Jr. et al. | |
| 7,341,587 B2 | 3/2008 | Molz, IV et al. | |
| 7,452,359 B1 | 11/2008 | Michelson | |
| 7,476,240 B2 | 1/2009 | Raymond et al. | |
| 7,497,869 B2 | 3/2009 | Justis | |
| 7,520,879 B2 | 4/2009 | Justis et al. | |
| 7,527,638 B2 | 5/2009 | Anderson et al. | |
| 7,572,276 B2 | 8/2009 | Lim et al. | |
| 7,578,822 B2 | 8/2009 | Rezach et al. | |
| 7,648,507 B2 | 1/2010 | Techiera et al. | |
| 7,666,189 B2 | 2/2010 | Gerber et al. | |
| 7,686,809 B2 | 3/2010 | Triplett et al. | |
| 7,708,763 B2 | 5/2010 | Selover et al. | |
| 7,717,944 B2 | 5/2010 | Foley et al. | |
| 7,749,232 B2 | 7/2010 | Salerni | |
| 7,758,584 B2 | 7/2010 | Bankoski et al. | |
| 7,758,617 B2 | 7/2010 | Iott et al. | |
| 7,776,051 B2 | 8/2010 | Colleran et al. | |
| 7,871,424 B2 | 1/2011 | Abdelgany | |
| 7,909,835 B2* | 3/2011 | Oribe et al. | 606/104 |
| 7,918,878 B2 | 4/2011 | Songer et al. | |
| 7,922,727 B2 | 4/2011 | Songer et al. | |
| 7,955,359 B2 | 6/2011 | Matthis et al. | |
| 7,967,821 B2 | 6/2011 | Sicvol et al. | |
| 7,967,826 B2 | 6/2011 | Colleran et al. | |
| 8,002,798 B2 | 8/2011 | Chin et al. | |
| 8,007,516 B2 | 8/2011 | Chao et al. | |
| 8,100,951 B2 | 1/2012 | Justis et al. | |
| 8,105,361 B2 | 1/2012 | Anderson et al. | |
| 8,192,439 B2 | 6/2012 | Songer et al. | |
| 8,192,440 B2 | 6/2012 | Jones et al. | |
| 8,197,488 B2 | 6/2012 | Sorrenti et al. | |
| 8,197,512 B1 | 6/2012 | Hunt et al. | |
| 8,202,304 B2 | 6/2012 | Boehm, Jr. et al. | |
| 8,206,395 B2* | 6/2012 | McLean et al. | 606/86 A |
| 8,211,145 B2 | 7/2012 | Dalton | |
| 8,235,997 B2* | 8/2012 | Hoffman et al. | 606/86 A |
| 8,277,491 B2 | 10/2012 | Selover et al. | |
| 8,343,160 B2 | 1/2013 | Techiera et al. | |
| 8,382,802 B2 | 2/2013 | Boehm, Jr. et al. | |
| 8,425,531 B2 | 4/2013 | Salerni | |
| 8,512,383 B2* | 8/2013 | McLean | 606/279 |
| 8,579,942 B2 | 11/2013 | Boehm, Jr. et al. | |
| 8,579,943 B2* | 11/2013 | Nichols et al. | 606/279 |
| 8,641,720 B2 | 2/2014 | Solitario, Jr. | |
| 2001/0021853 A1 | 9/2001 | Heckele et al. | |
| 2003/0100896 A1 | 5/2003 | Biedermann et al. | |
| 2005/0021040 A1 | 1/2005 | Bertagnoli | |
| 2005/0090824 A1 | 4/2005 | Shluzas et al. | |
| 2005/0171542 A1 | 8/2005 | Biedermann et al. | |
| 2005/0203516 A1 | 9/2005 | Biedermann et al. | |
| 2005/0203532 A1 | 9/2005 | Ferguson et al. | |
| 2005/0277934 A1 | 12/2005 | Vardiman | |
| 2007/0055241 A1 | 3/2007 | Matthis et al. | |
| 2007/0260246 A1 | 11/2007 | Biedermann | |
| 2008/0077138 A1 | 3/2008 | Cohen et al. | |
| 2008/0077139 A1 | 3/2008 | Landry et al. | |
| 2008/0077155 A1 | 3/2008 | Diederich et al. | |
| 2008/0119849 A1 | 5/2008 | Beardsley et al. | |
| 2008/0177270 A1 | 7/2008 | Sorrenti et al. | |
| 2008/0255567 A1 | 10/2008 | Accordino | |
| 2009/0012567 A1 | 1/2009 | Biedermann et al. | |
| 2009/0171391 A1 | 7/2009 | Hutton et al. | |
| 2009/0182382 A1 | 7/2009 | Justis et al. | |
| 2009/0209965 A1 | 8/2009 | Lewis | |
| 2009/0228052 A1 | 9/2009 | Beardsley et al. | |
| 2010/0024487 A1 | 2/2010 | Khoo et al. | |
| 2010/0030283 A1 | 2/2010 | King et al. | |
| 2010/0036443 A1 | 2/2010 | Hutton et al. | |
| 2010/0049206 A1 | 2/2010 | Biyani | |
| 2010/0131016 A1 | 5/2010 | Gerber et al. | |
| 2010/0145389 A1 | 6/2010 | Triplett et al. | |
| 2010/0249856 A1 | 9/2010 | Iott et al. | |
| 2010/0274252 A1 | 10/2010 | Bottomley et al. | |
| 2010/0314817 A1 | 12/2010 | Li et al. | |
| 2010/0331849 A1 | 12/2010 | Riesinger et al. | |
| 2010/0331901 A1 | 12/2010 | Iott et al. | |
| 2011/0015677 A1 | 1/2011 | Biedermann et al. | |
| 2011/0077690 A1 | 3/2011 | Shin et al. | |
| 2011/0093014 A1 | 4/2011 | Davis et al. | |
| 2011/0152940 A1 | 6/2011 | Frigg et al. | |
| 2011/0166610 A1 | 7/2011 | Altarac et al. | |
| 2011/0313464 A1 | 12/2011 | McLean | |
| 2012/0130429 A1 | 5/2012 | Mitchell et al. | |

FOREIGN PATENT DOCUMENTS

| | | |
|---|---|---|
| DE | 19549426 | 2/1997 |
| DE | 19754869 | 6/1999 |
| DE | 10011678 | 9/2001 |
| DE | 20310433 | 9/2003 |
| DE | 69433088 | 7/2004 |
| DE | 202004014120 | 11/2004 |
| EP | 0333990 | 9/1989 |
| EP | 0419564 | 4/1991 |
| EP | 0436697 | 7/1991 |
| EP | 0465158 | 1/1992 |
| EP | 0571619 | 12/1993 |
| EP | 0703757 | 4/1996 |
| EP | 0712607 | 5/1996 |
| EP | 0719118 | 7/1996 |
| EP | 0734703 | 10/1996 |
| EP | 0752830 | 1/1997 |
| EP | 0812167 | 12/1997 |
| EP | 0814718 | 1/1998 |
| EP | 0888099 | 1/1999 |
| EP | 1027004 | 8/2000 |
| EP | 1058520 | 12/2000 |
| EP | 1092395 | 4/2001 |
| EP | 1093760 | 4/2001 |
| EP | 1129668 | 9/2001 |
| EP | 1138267 | 10/2001 |
| EP | 1146821 | 10/2001 |
| EP | 1147751 | 10/2001 |
| EP | 1153574 | 11/2001 |
| EP | 1219248 | 7/2002 |
| EP | 1219268 | 7/2002 |
| EP | 1221901 | 7/2002 |
| EP | 1259198 | 11/2002 |
| EP | 1346695 | 9/2003 |
| EP | 1413257 | 4/2004 |
| EP | 1488755 | 12/2004 |
| EP | 1503684 | 2/2005 |
| EP | 1504732 | 2/2005 |
| EP | 1508307 | 2/2005 |
| EP | 1618848 | 1/2006 |
| EP | 1639954 | 3/2006 |
| EP | 1648316 | 4/2006 |
| EP | 1667616 | 6/2006 |
| EP | 1682022 | 7/2006 |
| EP | 1694225 | 8/2006 |
| EP | 1711112 | 10/2006 |
| EP | 1744694 | 1/2007 |
| EP | 1796560 | 6/2007 |
| EP | 1796565 | 6/2007 |
| EP | 1942821 | 7/2008 |
| EP | 1981411 | 10/2008 |
| EP | 1990016 | 11/2008 |

(56) References Cited

FOREIGN PATENT DOCUMENTS

| | | |
|---|---|---|
| EP | 1545355 | 12/2008 |
| EP | 2258292 | 12/2010 |
| EP | 1814476 | 5/2011 |
| EP | 2320819 | 5/2011 |
| EP | 1781194 | 12/2011 |
| EP | 1641403 | 1/2012 |
| EP | 1792588 | 12/2013 |
| EP | 2083719 | 6/2014 |
| GB | 2269753 | 2/1994 |
| GB | 2360215 | 9/2001 |
| RU | 2309707 | 11/2007 |
| WO | 89/12431 | 12/1989 |
| WO | 93/11715 | 6/1993 |
| WO | 94/10944 | 5/1994 |
| WO | 94/28824 | 12/1994 |
| WO | 95/26164 | 10/1995 |
| WO | 96/27321 | 9/1996 |
| WO | 96/27345 | 9/1996 |
| WO | 96/39988 | 12/1996 |
| WO | 97/31517 | 8/1997 |
| WO | 98/29047 | 7/1998 |
| WO | 99/15097 | 4/1999 |
| WO | 99/21500 | 5/1999 |
| WO | 99/21501 | 5/1999 |
| WO | 00/42898 | 7/2000 |
| WO | 00/67651 | 11/2000 |
| WO | 02/07624 | 1/2002 |
| WO | 03/007791 | 1/2003 |
| WO | 03/007829 | 1/2003 |
| WO | 03/008016 | 1/2003 |
| WO | 03/024298 | 3/2003 |
| WO | 03/057055 | 7/2003 |
| WO | 03/063714 | 8/2003 |
| WO | 03/094741 | 11/2003 |
| WO | 03/096917 | 11/2003 |
| WO | 2004/017837 | 3/2004 |
| WO | 2005/025461 | 3/2005 |
| WO | 2005/034781 | 4/2005 |
| WO | 2005/039392 | 5/2005 |
| WO | 2005/051247 | 6/2005 |
| WO | 2005/055868 | 6/2005 |
| WO | 2006/025919 | 3/2006 |
| WO | 2006/025921 | 3/2006 |
| WO | 2006/042188 | 4/2006 |
| WO | 2006/042335 | 4/2006 |
| WO | 2006/044920 | 4/2006 |
| WO | 2006/055448 | 5/2006 |
| WO | 2006/057837 | 6/2006 |
| WO | 2006/089085 | 8/2006 |
| WO | 2006/105068 | 10/2006 |
| WO | 2006/116544 | 11/2006 |
| WO | 2007/019391 | 2/2007 |
| WO | 2007/035326 | 3/2007 |
| WO | 2007/035441 | 3/2007 |
| WO | 2007/035892 | 3/2007 |
| WO | 2007/050640 | 5/2007 |
| WO | 2007/059207 | 5/2007 |
| WO | 2007/075375 | 7/2007 |
| WO | 2007/075791 | 7/2007 |
| WO | 2007/127918 | 11/2007 |
| WO | 2007/147093 | 12/2007 |
| WO | 2008/057506 | 5/2008 |
| WO | 2008/085445 | 7/2008 |
| WO | 2008/097974 | 8/2008 |
| WO | 2008/098054 | 8/2008 |
| WO | 2008/103781 | 8/2008 |
| WO | 2008/121613 | 10/2008 |
| WO | 2008/0136877 | 11/2008 |
| WO | 2008/149223 | 12/2008 |
| WO | 2009/017656 | 2/2009 |
| WO | 2009/025884 | 2/2009 |
| WO | 2009/052315 | 4/2009 |
| WO | 2009/055541 | 4/2009 |
| WO | 2009/056113 | 5/2009 |
| WO | 2009/064949 | 5/2009 |
| WO | 2009/067486 | 5/2009 |
| WO | 2009/094493 | 7/2009 |
| WO | 2011/002847 | 1/2011 |

* cited by examiner

SURGICAL INSTRUMENT

BACKGROUND OF THE INVENTIVE CONCEPTS

1. Field of the Inventive Concepts

The inventive concepts disclosed and claimed herein relate generally to surgical instruments, and more particularly, but not by way of limitation, to a surgical instrument for introducing a rod into a body and placing the rod in a minimally invasive manner.

2. Brief Description of Related Art

Traditional open surgical procedures in locations deep within a patient's body can result in extensive tissue traumatization, which in turn leads to prolonged recovery time and increased risk of infections. To reduce such trauma, laparoscopic surgical devices, remote-control instrument manipulation, minimal incision procedures, and the like have been developed. Such "minimally invasive" surgical procedures are especially desirable for spine surgeries because spine pathologies are located deep within the body without clear muscle planes, and there is danger of damaging the adjacent neural and vascular tissues.

Spine surgery often involves use of connecting elements, such as rods, screws, plates, or wires, which are placed and fixed between two or more locations of the spine. For example, spinal fixation is a neurosurgical procedure in which two or more vertebrae are anchored to each other to reduce vertebral mobility and to avoid potential damage to the spinal cord. Numerous spinal fixation devices and designs have been developed, but they typically all include combinations of rods, plates, and screws, and these devices must be transported through significant tissue without causing extensive tissue traumatization.

Placement of these connecting elements remains a challenging step in spine surgery, often requiring multiple incisions. Further difficulties arise due to the angle variation between, for example, an initial vertical insertion trajectory for a stabilization rod, and the desired final horizontal position of the rod.

In view of the foregoing, there is a need for surgical tools and methods that can avoid multiple incisions for rod insertion. There is also a need for surgical instruments that can provide a controlled rod insertion by allowing for changes in rod angulation with respect to the holding tool. It is to such a surgical instrument that the presently disclosed and claimed inventive concepts are directed.

BRIEF DESCRIPTION OF THE DRAWINGS

Like reference numerals in the figures represent and refer to the same or similar element or function. Implementations of the disclosure may be better understood when consideration is given to the following detailed description thereof. Such description makes reference to the annexed pictorial illustrations, schematics, graphs, and drawings. The figures are not necessarily to scale and certain features and certain views of the figures may be shown exaggerated, to scale or in schematic in the interest of clarity and conciseness. In the drawings.

DETAILED DESCRIPTION OF EXEMPLARY EMBODIMENTS

Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

References to orthopedic or spinal surgery methods and rods are for example only, and the inventive concepts can be used with any surgical procedure requiring insertion and/or placement of a rod shaped article within a patient's body.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Figure 11:
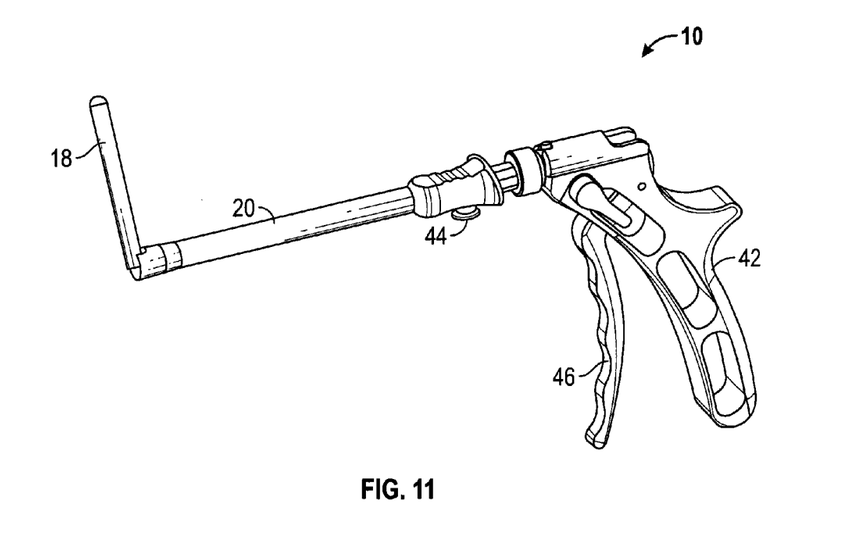
FIG. 11 is a perspective view of the surgical instrument shown with a handle and holding a rod.
Figure 12:
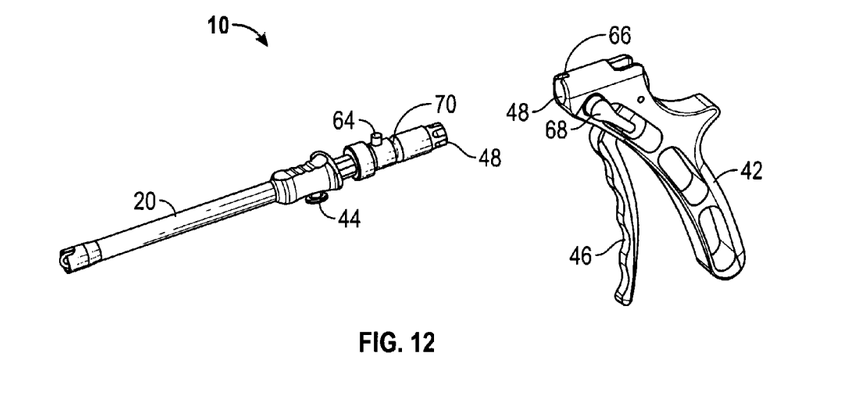
FIG. 12 is an exploded perspective view of the surgical instrument.

Referring now to the drawings, and more particularly to FIGS. 1A, 1B, 11 and 12, shown therein is an exemplary embodiment of a surgical instrument 10 constructed in accordance with the inventive concepts disclosed and claimed herein. The surgical instrument 10 includes a rod holder 12, a sleeve 20 disposed about the rod holder 12, and a pusher rod 22 disposed within the rod holder 12. The surgical instrument 10 may further include a handle 42 (FIGS. 11 and 12). The surgical instrument 10 can be used by a surgeon to insert and place a rod 18 (FIG. 11) in a patient's body while allowing variation of the angulation of the rod before and during rod insertion and placement.

Components of the surgical instrument can be made of materials including, but not limited to, titanium, titanium alloys, stainless steel, ceramics, and/or polymers. Some components may be autoclaved and/or chemically sterilized. Components that cannot be autoclaved and/or chemically sterilized may be made of sterile materials.

Figure 4:
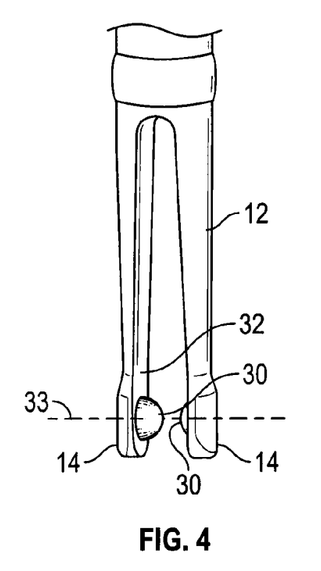
FIG. 4 is a perspective view of a portion of a rod holder.

The rod holder 12 is hollow and has a pair of opposing yieldable tines 14 for releasably gripping at least a first end 16 of a rod 18. As best illustrated in FIGS. 1B and 4, each of the tines 14 of the rod holder 12 has an inwardly extending detent 30 on an inner surface 32. The detents 30 are shaped so that the first end 16 of the rod 18 is pivotably engageable with the rod 18 as shown, for example, in FIG. 5. The detents 30 are in axial alignment with one another so as to define a pivot axis 33 (FIG. 4) located between the centers of the two detents 30. The rod 18 is rotatable about the pivot axis 33. The detents 30 can be spherical, or a partial sphere, pin, cone, or other shape allowing pivotal motion of the rod 18 held between the tines 14.

Figure 6:
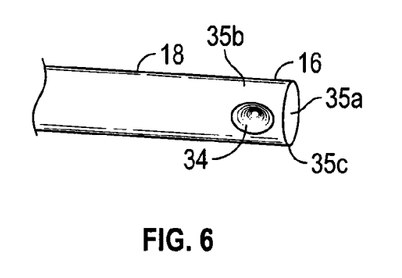
FIG. 6 is a perspective view of a portion of a rod.

As best shown in FIG. 6, the rod 18 may include a pair of recesses 34 (only one of the recesses 34 visible) shaped to receive the detent 30. The design and dimensions of the detents 30, recesses 34, and tines 14, and the spring strength of the tines, can be selected to allow for a secure hold on the rod 18 while providing an easy "snap" when the rod 18 and tines 14 are coupled. The snap provides the user with a positive feedback indicating successful coupling.

It will be understood that the positioning of the detents and the recesses can be reversed where recesses are positioned on the inner surface 32 of the rod holder 12 and shaped to receive the detents present on the rod 18. In this embodiment, the axial alignment of the centers of the two recesses 34 defines the pivot axis 33 about which the rod 18 is rotatable. The first end 16 of the rod 18 is substantially cylindrical in shape where the rod 18 has a flat end surface 35a and a convex side surface 35b which intersect one another to define a curved edge 35c.

Figure 7:
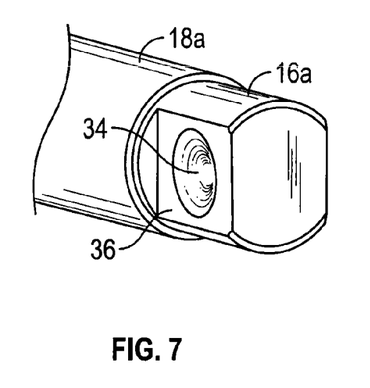
FIG. 7 is a perspective view of a portion of another embodiment of a rod.
Figure 8:
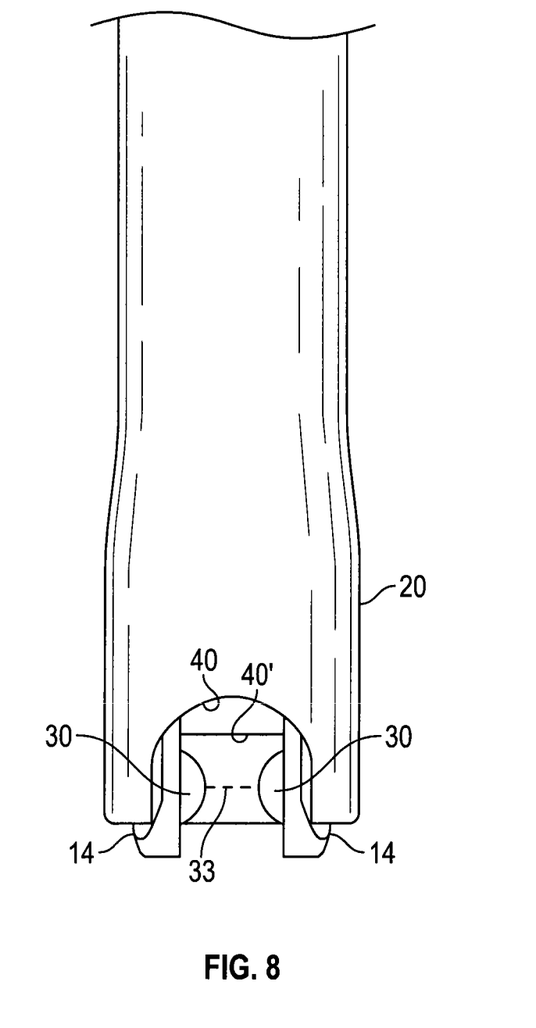
FIG. 8 is an elevational view of a portion of the surgical instrument shown with a sleeve in an extended position.

FIG. 7 illustrates another embodiment of a rod 18a with a first end 16a. The first end 16a is similar to the first end 16 of the rod 18 except that the first end 16a of the rod 18a has two opposing flat faces 36 with a recess 34a provided on each of the flat faces 36. The flat faces 36 result in the first end 16a of the rod 18a having reduced diameter which in turn allows the rod holder 12 to be reduced in diameter.

Figure 3A:
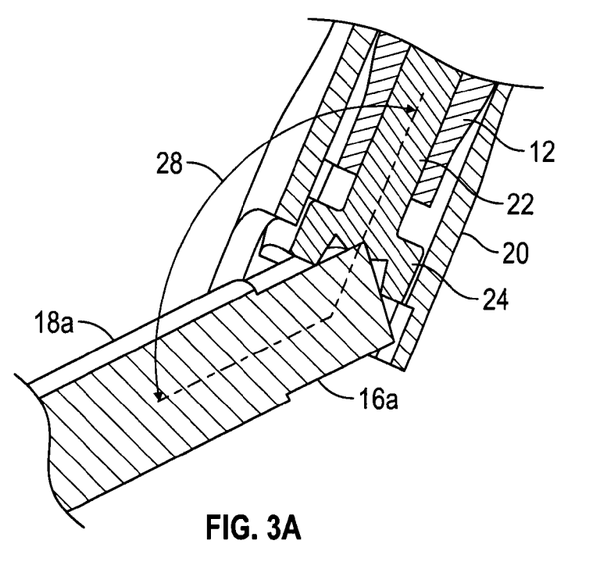
FIG. 3A is a sectional view of the surgical instrument shown with a pusher rod engaged with a rod.
Figure 3B:
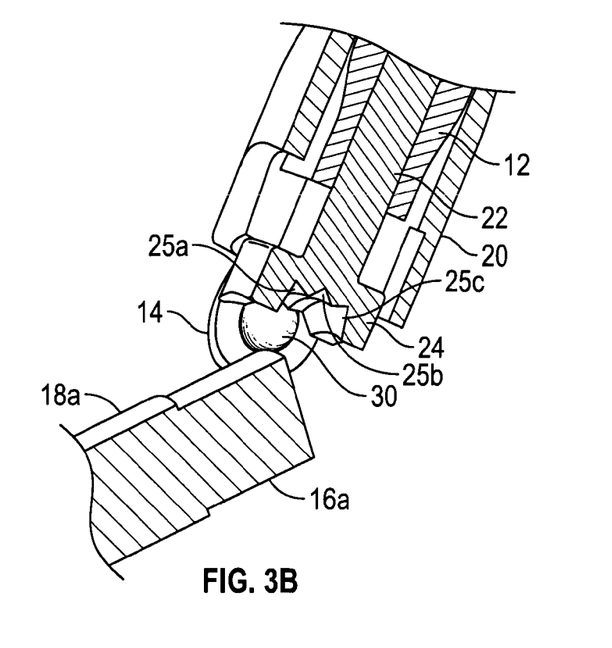
FIG. 3B is a sectional view of the surgical instrument shown with the rod released from the rod holder and the pusher rod in an extended position.

Referring to FIGS. 3A and 3B, the sleeve 20 is disposed about the rod holder 12 and is slideable between an extended position (FIG. 3A) and a retracted position (FIG. 3B). In the extended position, the sleeve 20 is disposed about the tines 14 so as to hold the tines 14 in a rod gripping position when the rod 18 is positioned between the tines 14. In the retracted position, the sleeve 20 is retracted from the tines 14 leaving the tines 14 outwardly moveable to permit release of the rod 18 from the tines 14.

Figure 1A:
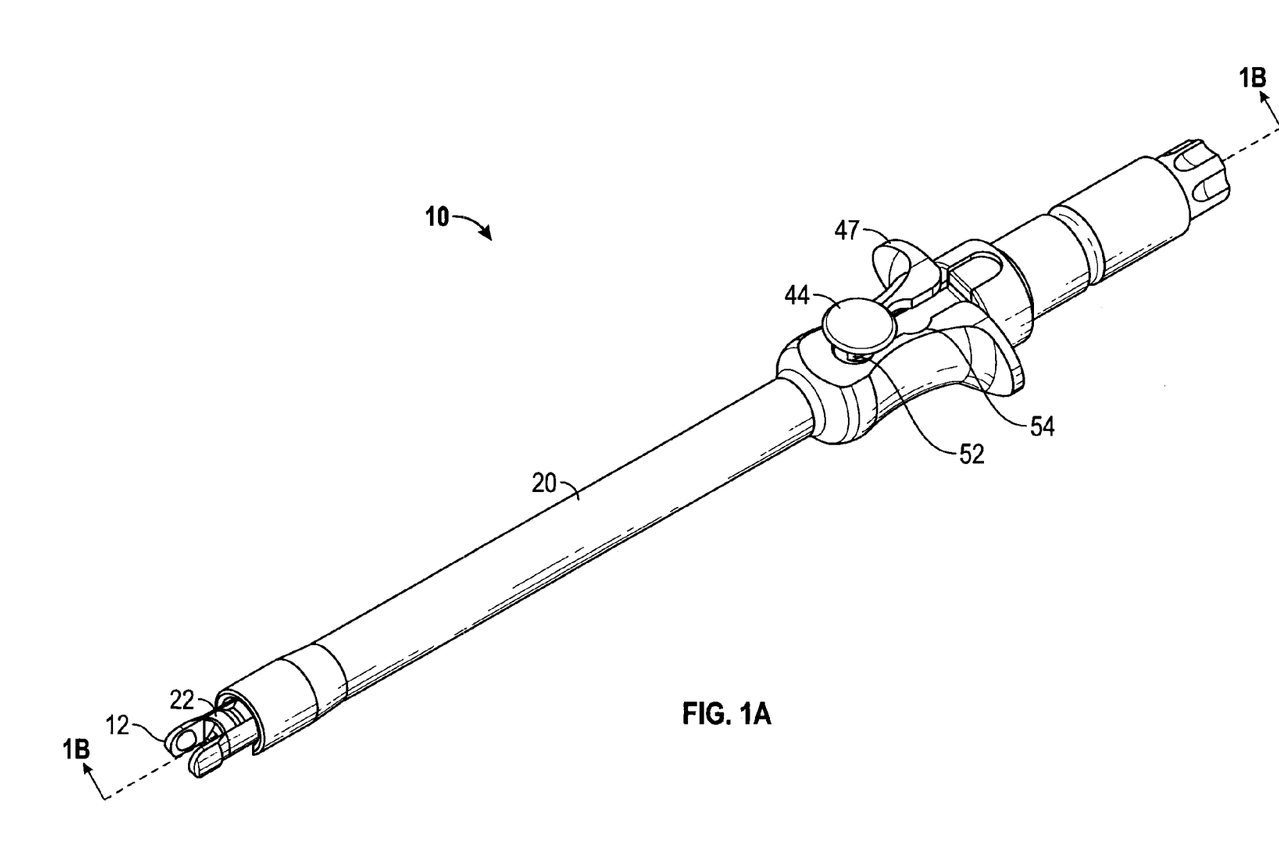
FIG. 1A is a perspective view of a surgical instrument constructed in accordance with the inventive concepts disclosed herein.
Figure 1B:
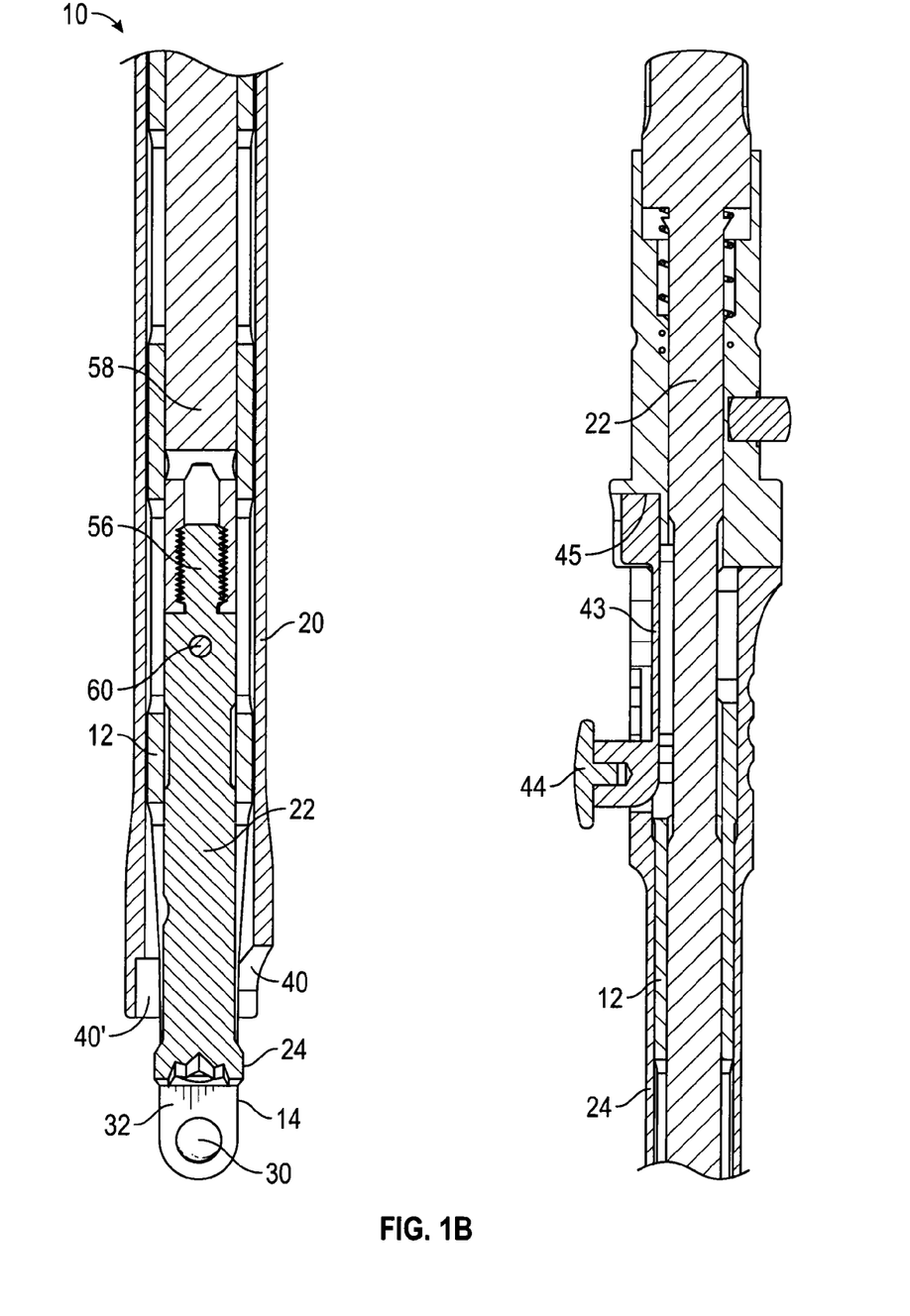
FIG. 1B is a sectional view taken along line 1B-1B of FIG. 1A.
Figure 14:
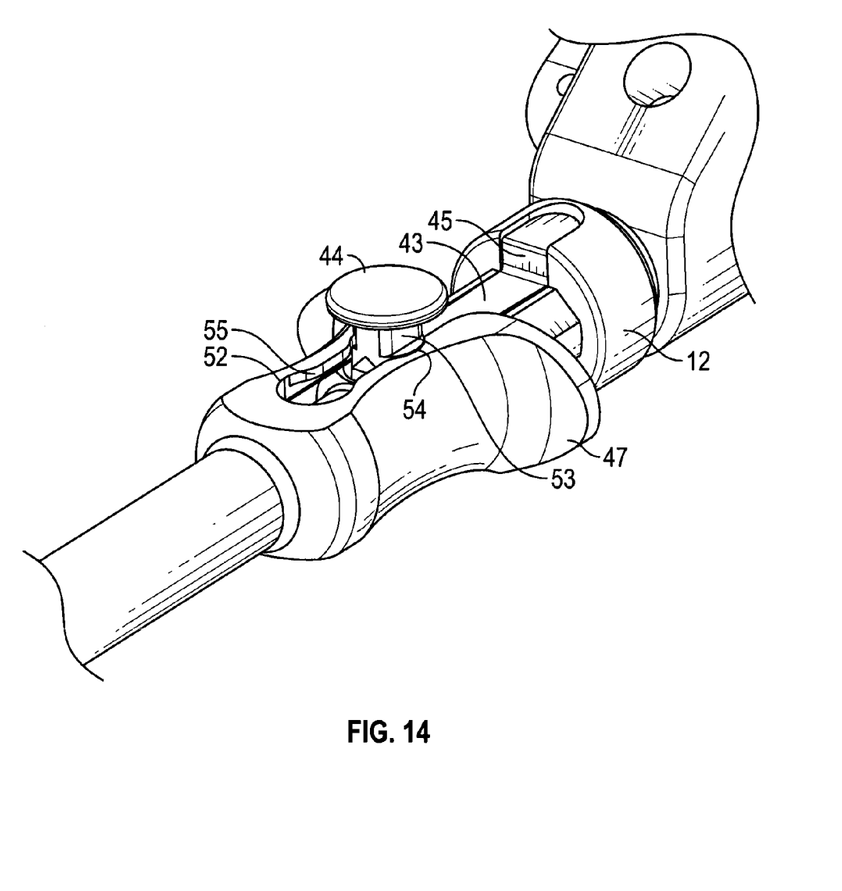
FIG. 14 is a perspective view of a portion of the surgical instrument illustrating a sleeve catch.

Referring now to FIGS. 1A and 14, the position of the sleeve 20 with respect to the rod holder 12 is adjusted with a sleeve handle 47 provided on a proximal end of the sleeve 20. The position of the sleeve 20 with respect to the rod holder 12 may be maintained using a spring plate 43 having a proximal end 45 attached to the rod holder 12. A push knob 44 attached to a distal end of the spring plate 43 can be depressed to align a narrowing 53 in the push knob 44 with a neck 55 of the sleeve handle 42, thereby allowing movement of the sleeve handle 42 to reposition the push knob 44 between a first aperture 52 and a second aperture 54, thereby moving the sleeve 20 between the retracted and extended positions, respectively.

Referring now to FIGS. 1B, 8 and 9A-9D, the sleeve 20 is provided with notches 40 and 40' to allow the rod 18 to pivot while secured to the rod holder 12 by the sleeve 20. In one embodiment (not shown), the notch 40' has substantially the same shape as the notch 40, thereby allowing the rod 18 to pivot 180°. In many instances, only a 90° pivot or less is necessary, and greater rod gripping strength may be provided when the size of the notch 40' is minimized to allow rotation only through the notch 40. For example, as shown in FIGS. 1B, 8 and 9A-9D, the notch 40' does not extend through the thickness of the sleeve. In one embodiment, the shape of the notch 40 is made to receive and cradle the rod 18 when the rod 18 is positioned at a 90° angle 28 with respect to the pusher rod 22.

When the sleeve 20 is in the extended position, the rotational position of the sleeve 20 with respect to the rod holder 12 is such that the notch 40 is positioned along the axis 33 connecting the centers of the two detents 30. This position is maintained by the push knob 45 on the rod holder 12 being restricted to either the first or second apertures 52 and 54, respectively, on the sleeve 20.

Figure 5:
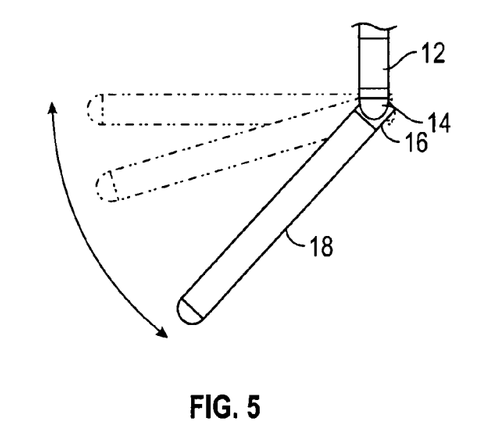
FIG. 5 is an elevational view illustrating movement of the rod relative to the rod holder.

The pusher rod 22 is disposed within the rod holder 12 and has a distal end 24 provided with a plurality of rod receiving notches 25a-25c. The pusher rod 22 is slideable between a retracted position, a holding position, and an extended position. In the retracted position, the distal end 24 of the pusher rod 22 is positioned so as to disengage from the rod 18 and permit the rod 18 to freely pivot relative to the rod holder 12, as shown in FIG. 5. In the holding position (FIGS. 3A and 9A-9D), the distal end 24 of the pusher rod 22 is positioned to engage the first end 16 of the rod 18 when the rod 18 is positioned between the tines 14 of the rod holder 12. In the extended position (FIG. 3B), the distal end 24 of the pusher rod 22 is positioned to push and release the rod 18 from the tines 14 of the rod holder 12.

Each of the rod receiving notches 25a-25c is configured to matingly engage at least a portion of the first end 16 of the rod 18, as illustrated by way of example in FIGS. 3A and 9A-9D, in such a way that when the rod 18 is gripped by the tines 14 of the rod holder 12 with the sleeve 20 in the extended position and the distal end 24 of the pusher rod 22 is in engagement with the first end 16 of the rod 18, the rod 18 is held at a selected angle 28 with respect to the pusher rod 22 dependent upon in which of the rod receiving notches 25a-25c the rod 18 is disposed. In the exemplary embodiment, the rod receiving notches 25a-25c are configured to engage with a portion of the rod 18 one at a time.

As best shown in FIGS. 9A-9D and 10, the rod receiving notches 25a-25c are each defined by a pair of notch surfaces 26a and 26b formed at an angle relative to one another which substantially matches the angle between the end surface 35a and the side surface 35b of the rod 18. To this end, the angle between the notch surfaces 26a and 26b can vary depending on the angle between the end surface 35a and the side surface 35b of the rod 18. In one exemplary embodiment, the angle between the notch surfaces 26a and 26b is about 90 degrees.

The notch surface 26a and 26b are configured to conform to the contour of a corresponding surface of the rod 18. With the embodiments of the rods 18 and 18a illustrated in FIGS. 6 and 7, respectively, the notch surfaces 26a are concave in shape to correspond to the shape of the curved side surface 35b, and the notch surfaces 26b are substantially flat to correspond to the shape of the end surface 35a.

The intersection of the notch surfaces 26a and 26b defines a trough line 26c. The trough lines 26c of the rod receiving notches 25a-25c are parallel to one another. Due to the shapes of the notch surfaces 26a and 26b, the trough lines 26c are curvilinear or concave in shape so as to correspond to the curved shape of the edge 35c of the rod 18.

To accommodate various positions of the rod 18, the rod receiving notches 25a-25c are provided in the distal end 24 of the pusher rod 22 so that the rod receiving notches 25a-25c are radially oriented about the rod pivot axis 33 at equal angular intervals when the pusher rod 18 is in the holding position. It should be appreciated that while the pusher rod 22 is illustrated as having three rod receiving notches, the number of rod receiving notches may be varied from one, two, three, or more.

Figure 9A:
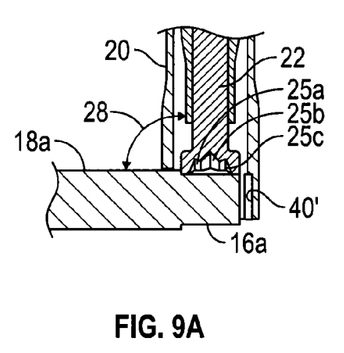
FIGS. 9A-9D are sectional views showing the rod held at different selected angles by the surgical instrument.
Figure 10:
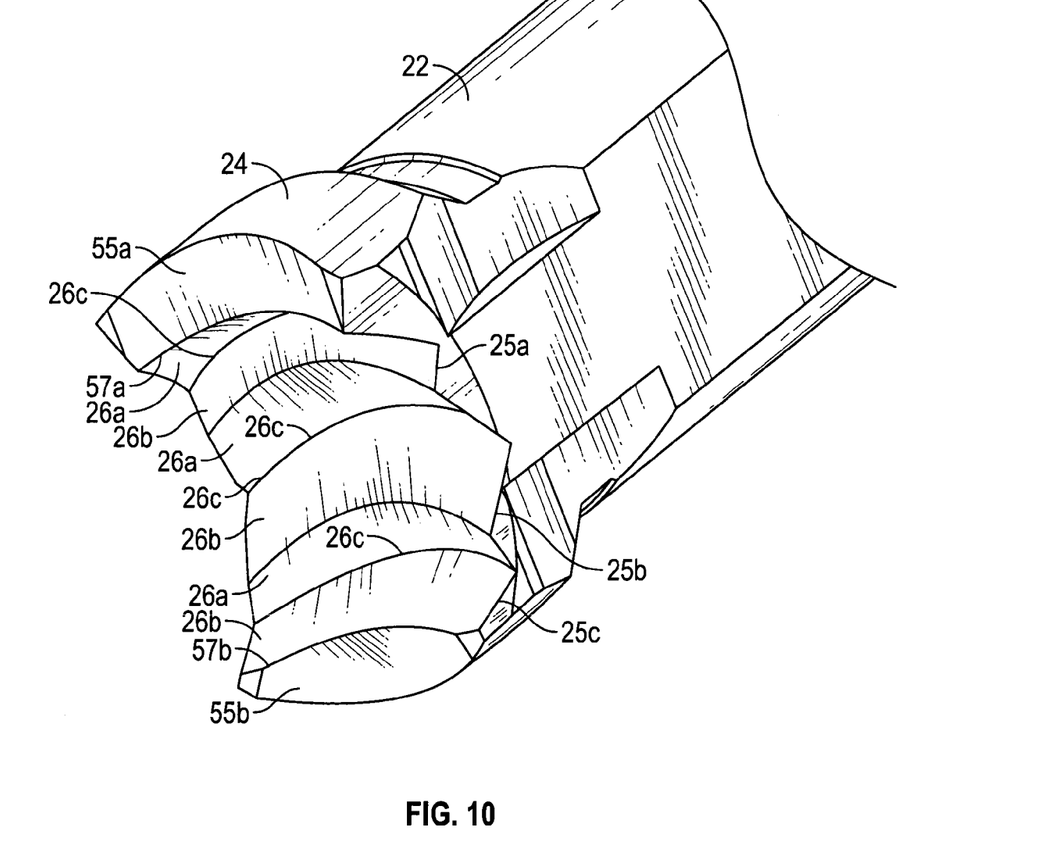
FIG. 10 is a perspective view of a distal end of the pusher rod.

To support the rod 18 at a 90 degree angle relative to the pusher rod 22, the distal end 24 of the pusher rod 22 is provided with a pair of lateral end surfaces 55a and 55b (FIG. 10). The lateral end surfaces 55a and 55b are arranged in a diametrically opposing relationship with another and configured to conform to the contour of the side surface 35b of the rod 18 so as to matingly engage the rod 18 when the rod 18 is positioned at a 90 degree angle relative to the pusher rod 22 (FIG. 9A). More particularly, the lateral end surfaces 55 are concave in shape to mate with the convex shape of side surface 35b of the rod 18.

Figure 9B:
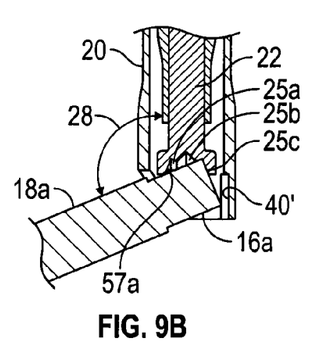
Figure 9C:
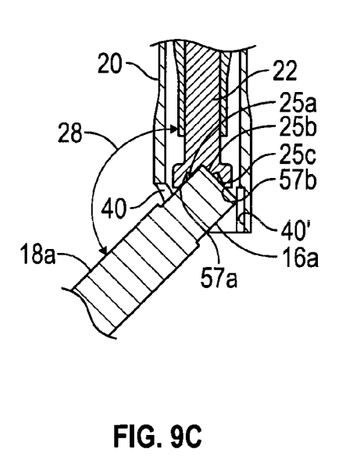
Figure 9D:
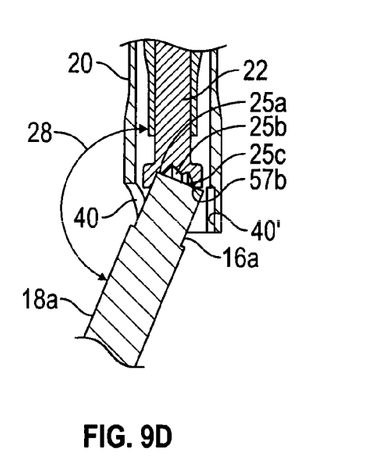

To provide further support to the rod 18, the distal end 24 of the pusher rod 22 may be configured to contact the rod 18 at multiple points. In particular, the lateral end surface 55a intersects the notch surface 26a of the rod receiving notch 25a to define an edge 57a, and the lateral end surface 55b intersects the notch surface 26b of the rod receiving notch 25c to define and edge 57b. The edges 57a and 57b are in a diametrically opposing relationship with another. As illustrated in FIGS. 9B and 9C, the notch surface 26a of the rod receiving notch 25b and the notch surface 26a of the rod receiving notch 25c are in alignment with the edge 57a. As such, the side surface 35b of the rod 18 contacts at least a portion of the edge 57a when the rod 18 is positioned in the rod receiving notch 25b and the rod receiving notch 25c to provide another point of supporting contact between the pusher rod 22 and the rod 18. Similarly, the notch surface 26b of the rod receiving notch 25a and the notch surface 26b of the rod receiving notch 25b are in alignment with the edge 57b. As such, the end surface 35a of the rod 18 contacts at least a portion of the edge 57b when the rod 18 is positioned in the rod receiving notch 25a and the rod receiving notch 25b to provide another point of supporting contact between the pusher rod 22 and the rod 18.

Figure 2:
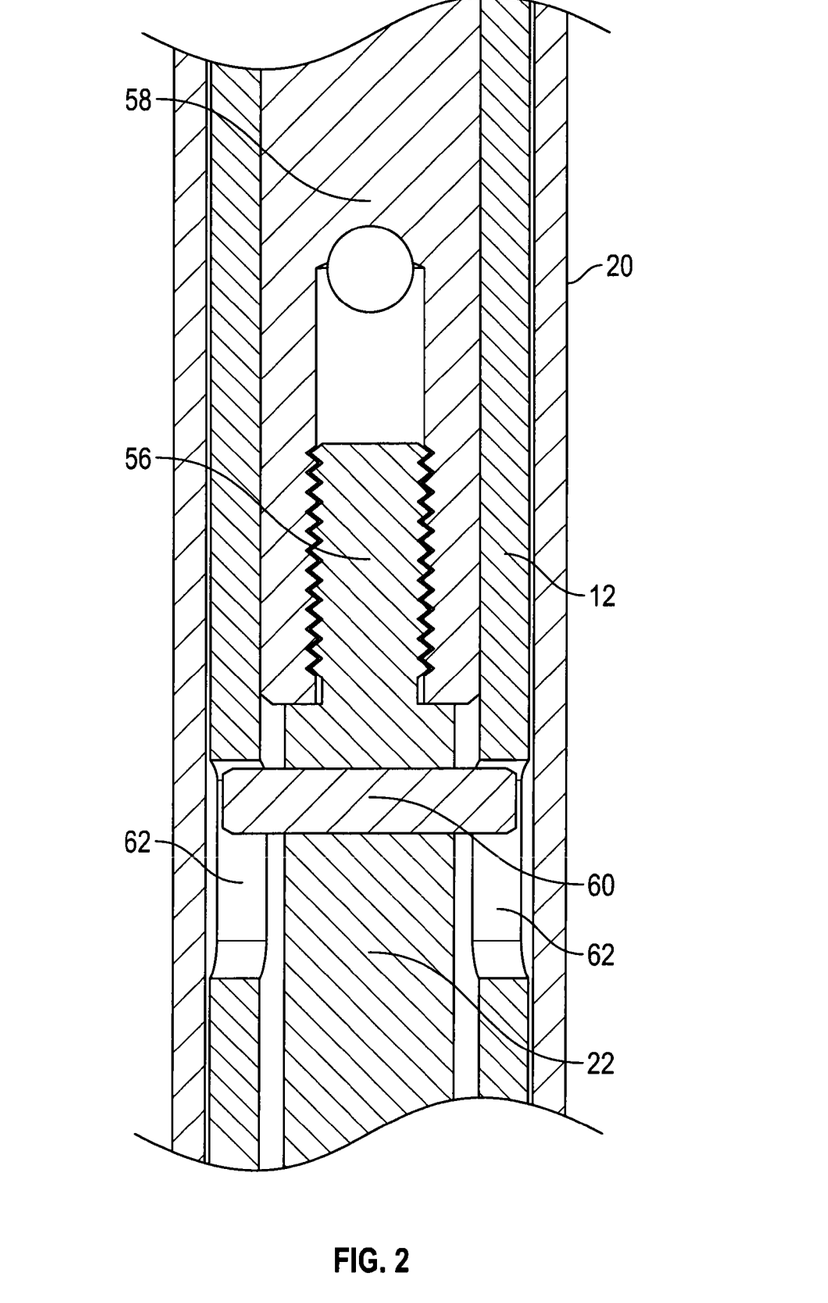
FIG. 2 is a sectional view of a portion of the surgical instrument.

As illustrated in FIG. 2, the pusher rod 18 may include a first section 56 that is threadingly engageable with a second section 58 to facilitate disassembling and cleaning. A pin 60 extending from the pusher rod 22 is slideably positioned in slots 62 in the rod holder 12 to maintain the rotational position of the pusher rod 22 with respect to the rod holder 12.

Figure 13:
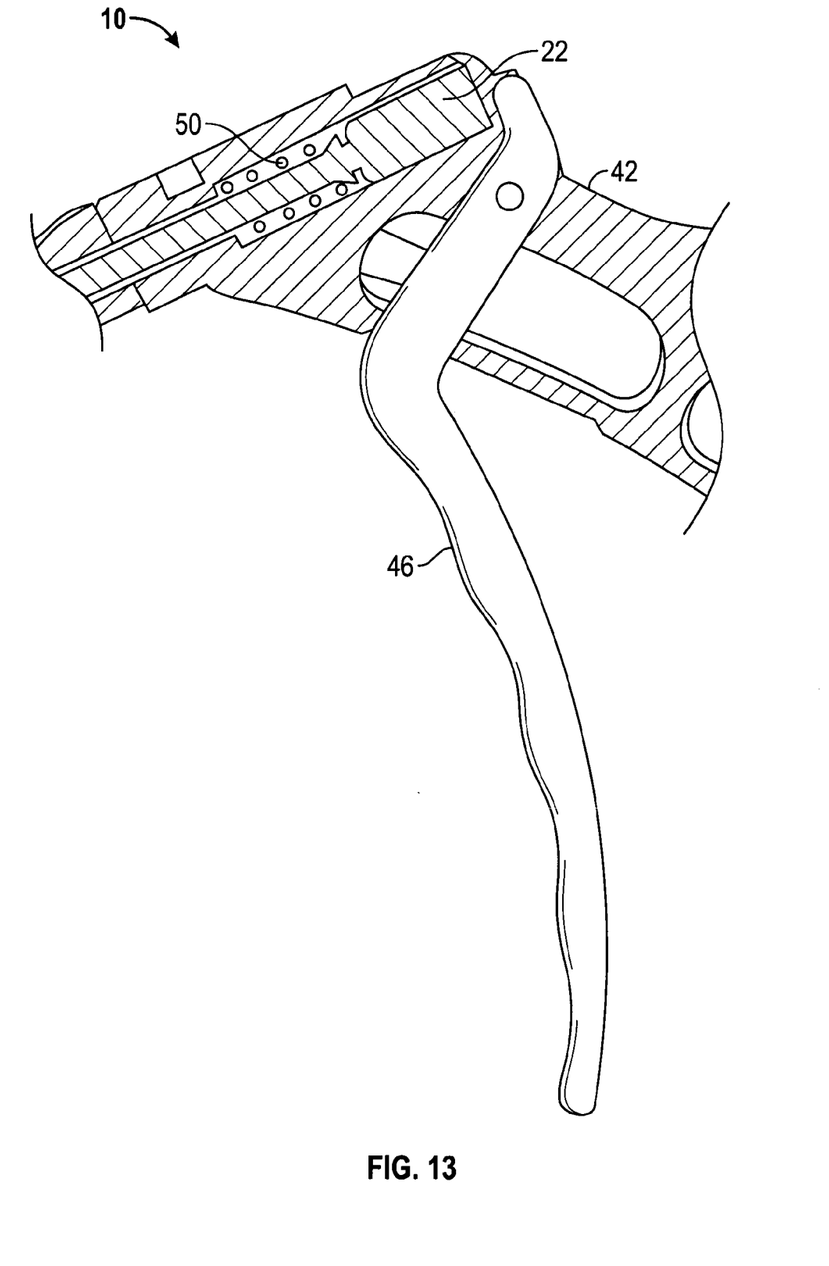
FIG. 13 is a sectional view of a portion of the surgical instrument showing a lever of the handle in association with the pusher rod.

Referring now to FIGS. 11-13, the handle 42 facilitates a surgeon in inserting and positioning the rod 18 during surgery. The handle 42 may be connected to a proximal end of the rod holder 12 and be provided with a lever 46 for pushing the rod 18 from the rod holder 12. A spring 50 is provided to bias the pusher rod 22 in the retracted position. By maintaining pressure on the lever 46, the surgeon can keep the pusher rod engaged with the rod 18. By releasing pressure on the lever 46, the pusher rod 22 is retracted by the spring 50 and the rod 18 is allowed to pivot. With the sleeve 20 in the retracted position, the lever 46 of the handle 42 can be used to push the pusher rod 22 toward the extended position disengaging the rod 18 from the rod holder 12. The rod holder 12 can then be pulled away from the rod 18 at any angulation.

The handle 42 can be connected to the rod holder 12 using cylindrical opposing surfaces as shown in FIG. 12, allowing the handle 42 to be readily connected and removed from the rod holder 12. To insure the proper orientation of the handle 42, an orientation mark 64 on the rod holder 12 can be positioned in a respective opening 66 on the handle 42. An eccentric (not shown) on a locking lever 68 on the handle 42 can be used to engage a groove 70 on the rod holder 12 and lock the handle 42 onto the surgical instrument 10. By disengaging the locking lever 68 from the groove 70, the handle 42 can be readily removed.

During surgery, following the first rod insertion, the handle 42 can be connected to a second rod holder 12 in order to insert a contra lateral rod 18. Both rod holders 12 can be disconnected after the entire construct is finished. When the handle 42 is disconnected, the rod holder 12 can be held in one hand and pulled away from the rod 18 in a manner similar to a syringe.

During the insertion process of surgery, a surgeon will be able to modify the angulation of the rod 18 in order to optimize the insertion trajectory and to minimize the strain on the soft tissue. The surgical instrument 10 can be used in any surgical indication requiring stabilization using screw and rod type constructs. The presently disclosed surgical instrument 10 can be used in open or minimally invasive surgeries. Additional incisions for the rod insertion are avoided and a controlled rod insertion is provided by allowing changes of the rod angulation with respect to the rod holder.

From the above description, it is clear that the inventive concepts disclosed herein are well adapted to carry out the objects and to attain the advantages mentioned herein as well as those inherent in the inventive concepts disclosed herein. While exemplary embodiments of the inventive concepts disclosed herein have been described for purposes of this disclosure, it will be understood that numerous changes may be made which will readily suggest themselves to those skilled in the art and which are accomplished without departing from the scope of the inventive concepts disclosed herein and defined by the appended claims.

What is claimed is:

1. A surgical instrument, comprising:
a rod holder having a pair of opposing yieldable tines configured to releasably grip a rod therebetween;
a sleeve disposed about the rod holder and slideable between an extended position wherein the sleeve is positioned about the tines so as to hold the tines in a rod gripping position when the rod is positioned between the tines, and a retracted position wherein the sleeve is positioned such that the tines are outwardly moveable to permit release of the rod from the tines; and
a pusher rod slidably disposed within the rod holder, the pusher rod having a distal end with a plurality of rod receiving notches configured to engage at least a portion of one end of the rod in such a way that when the rod is gripped by the tines of the rod holder with the sleeve in the extended position and the distal end of the pusher rod is in engagement with the end of the rod, the rod is held at a selected angle with respect to the pusher rod.

2. The surgical instrument of claim 1, wherein each of the rod receiving notches is defined by at least a pair of notch surfaces formed at an angle relative to one another, wherein the notch surfaces intersect to define a trough line, and wherein the trough lines of the rod receiving notches are parallel to one another.

3. The surgical instrument of claim 2, wherein the trough line of the rod receiving notches is curvilinear.

4. The surgical instrument of claim 3, wherein the trough line of the rod receiving notches is concave.

5. The surgical instrument of claim 2, wherein the angle between the notch surfaces is about 90 degrees.

6. The surgical instrument of claim 2, wherein the pair of notch surfaces is configured to conform to the contour of a corresponding surface of the rod.

7. The surgical instrument of claim 5, wherein one of the notch surfaces is concave and wherein the other notch surface is substantially flat.

8. The surgical instrument of claim 1, wherein the rod receiving notches are radially oriented.

9. The surgical instrument of claim 1, wherein the tines cooperate to define a rod pivot axis and wherein the rod receiving notches are radially oriented about the rod pivot axis when the pusher rod is in the holding position.

10. The surgical instrument of claim 1, wherein each of the rod receiving notches is defined by at least a pair of notch surfaces formed at an angle relative to one another, wherein the distal end of the pusher rod has a pair of diametrically opposed edges, and wherein one of the notch surfaces of each of the rod receiving notches is aligned with at least a portion of one of the edges and the other notch surface of each of the rod receiving notches is aligned with at least a portion of the other edge.

11. The surgical instrument of claim 10, wherein the pusher rod has three rod receiving notches.

12. The surgical instrument of claim 1, wherein each of the tines has an inwardly extending detent pivotally engageable with the first end of the rod, and wherein each of the detents is in axial alignment with one another so as to define a pivot axis.

13. The surgical instrument of claim 1, wherein the pusher rod is slideable between a retracted position wherein the distal end of the pusher rod is positioned so as to be disengaged from the rod to permit the rod to pivot relative to the rod holder, a holding position wherein the distal end of the pusher rod is positioned to engage the first end of the rod, and an extended position wherein the distal end of the pusher rod is positioned to cause the rod to release from the tines of the rod holder.

14. The surgical instrument of claim 13, wherein the pusher rod is biased toward the retracted position.

15. The surgical instrument of claim 1, further comprising a handle attached to the rod holder.

16. The surgical instrument of claim 15, wherein the handle is detachable from the rod holder.

17. The surgical instrument of claim 15, wherein the handle has a lever in association with the pusher rod to move the pusher rod from the retracted position to the holding position and the extended position.

18. A surgical instrument, comprising:
a rod holder having a pair of opposing yieldable tines configured to releasably grip at least at least one end of a rod therebetween; and
a pusher rod disposed within the rod holder and slideable between a retracted position wherein a distal end of the pusher rod is positioned so as to be disengaged from the rod to permit the rod to pivot relative to the rod holder, a holding position wherein the distal end of the pusher rod is positioned to engage the first end of the rod, and an extended position wherein the distal end of the pusher rod is positioned beyond the holding position to push and thereby release the rod from the tines of the rod holder, the distal end of the pusher rod having a plurality of rod receiving notches configured to engage the first end of the rod in such a way that when the rod is gripped by the tines of the rod holder and the distal end of the pusher rod is engaged with the end of the rod in the holding position, the rod is held at a selected angle with respect to the pusher rod.

19. The surgical instrument of claim 18, wherein each of the rod receiving notches is defined by at least a pair of notch surfaces formed at an angle relative to one another, wherein the notch surfaces intersect to define a trough line, and wherein the trough lines of the rod receiving notches are parallel to one another.

20. The surgical instrument of claim 19, wherein the trough line of the rod receiving notches is curvilinear.

21. The surgical instrument of claim 20, wherein the trough line of the rod receiving notches is concave.

22. The surgical instrument of claim 19, wherein the angle is about 90 degrees.

23. The surgical instrument of claim 19, wherein the pair of notch surfaces is configured to conform to the contour of a corresponding surface of the rod.

24. The surgical instrument of claim 23, wherein one of the notch surfaces is concave and wherein the other notch surface is substantially flat.

25. The surgical instrument of claim 18, wherein the rod receiving notches are radially oriented.

26. The surgical instrument of claim 18, wherein the tines cooperate to define a rod pivot axis and wherein the rod receiving notches are radially oriented about the rod pivot axis when the pusher rod is in the holding position.

27. The surgical instrument of claim 18, wherein each of the rod receiving notches is defined by at least a pair of notch surfaces formed at an angle relative to one another, wherein the distal end of the pusher rod has a pair of diametrically opposed edges, and wherein one of the notch surfaces of each of the rod receiving notches is aligned with at least a portion of one of the edges and the other notch surface of each of the rod receiving notches is aligned with at least a portion of the other edge.

28. The surgical instrument of claim 27, wherein the pusher rod has three rod receiving notches.

29. The surgical instrument of claim 18, wherein each of the tines has a detent pivotally engageable with the first end of a rod, the detents in axial alignment with one another so as to define a pivot axis.

30. The surgical instrument of claim 18, wherein the pusher rod is biased toward the retracted position.

31. The surgical instrument of claim 18, further comprising a handle attached to the rod holder.

32. The surgical instrument of claim 31, wherein the handle has a lever in association with the pusher rod to move the pusher rod from the retracted position to the holding position and the extended position.

33. A surgical kit, comprising:

at least one rod;

a rod holder having a pair of opposing yieldable tines configured to releasably grip at least one end of the rod therebetween;

a sleeve disposed about the rod holder and slideable between an extended position wherein the sleeve is positioned about the tines so as to hold the tines in a rod gripping position when the rod is positioned between the tines, and a retracted position wherein the sleeve is positioned such that the tines are outwardly moveable to permit release of the rod from the tines; and a pusher rod disposed within the rod holder and slideable between a retracted position wherein a distal end of the pusher rod is positioned so as to be disengaged from the rod to permit the rod to pivot relative to the rod holder, a holding position wherein the distal end of the pusher rod is positioned to engage the end of the rod, and an extended position wherein the distal end of the pusher rod is positioned beyond the holding position to push and thereby release the rod from the tines of the rod holder, the distal end of the pusher rod having a plurality of rod receiving notches configured to engage at least a portion of the end of the rod in such a way that when the rod is gripped by the tines of the rod holder and the distal end of the pusher rod is in engagement with the end of the rod in the holding position, the rod is held at a selected angle with respect to the pusher rod.

34. The surgical kit of claim 33, wherein the end of the rod has an end surface and a side surface oriented relative to the end surface to define an edge, wherein each of the rod receiving notches is defined by at least a pair of notch surfaces configured and angled relative to one another to define a trough line and matingly engage the end of the rod.

35. The surgical kit of claim 34, wherein the edge of the rod is curved, and wherein the trough lines of the rod receiving notches are curved to correspond to the curve of the edge of the rod.

36. The surgical kit of claim 35, wherein the trough line of the rod receiving notches is concave.

37. The surgical kit of claim 34, wherein the angle between the notch surfaces is about 90 degrees.

38. The surgical kit of claim 34, wherein the pair of notch surfaces is configured to conform to the contour of the end surface and the side surface of the rod.

39. The surgical kit of claim 38, wherein the end surface of the rod is substantially flat and the side surface of the rod is convex, and wherein one of the notch surfaces is concave and wherein the other notch surface is substantially flat.

40. The surgical kit of claim 33, wherein the rod receiving notches are radially oriented.

41. The surgical kit of claim 33, wherein the tines cooperate to define a rod pivot axis and wherein the rod receiving notches are radially oriented about the rod pivot axis when the pusher rod is in the holding position.

42. The surgical kit of claim 33, wherein each of the rod receiving notches is defined by at least a pair of notch surfaces formed at an angle relative to one another, wherein the distal end of the pusher rod has a pair of diametrically opposed edges, and wherein one of the notch surfaces of each of the rod receiving notches is aligned with at least a portion of one of the edges and the other notch surface of each of the rod receiving notches is aligned with at least a portion of the other edge.

43. The surgical kit of claim 42, wherein the pusher rod has three rod receiving notches.

44. The surgical kit of claim 33, wherein each tine has a detent pivotally engageable with the first end of the rod.

45. The surgical kit of claim 33, wherein the pusher rod is biased toward the retracted position.

46. The surgical kit of claim 33, wherein at least one end of the rod is configured to pivotally engage the tines of the rod holder.

47. The surgical kit of claim 33, further comprising a handle attached to the rod holder, wherein the handle is provided with a lever in association with the pusher rod to move the pusher rod from the retracted position to the holding position and the extended position.

48. The surgical kit of claim 33, wherein the rod receiving notches engage with the rod one at a time.

* * * * *